United States Patent [19]

Renson et al.

[11] 4,352,799

[45] Oct. 5, 1982

[54] 2-PHENYL-1,2-BENZISOSELENAZOL-3(2H)-ONE CONTAINING PHARMACEUTICAL PREPARATIONS AND PROCESS FOR THE TREATMENT OF RHEUMATIC DISEASES

[75] Inventors: Marcel Renson, Jupille, Belgium; Eugen Etschenberg; Johannes Winkelmann, both of Cologne, Fed. Rep. of Germany

[73] Assignee: A. Nattermann & Cie GmbH, Cologne, Fed. Rep. of Germany

[21] Appl. No.: 281,876

[22] Filed: Jul. 9, 1981

[30] Foreign Application Priority Data

Jul. 17, 1980 [DE] Fed. Rep. of Germany ....... 3027073

[51] Int. Cl.³ .............................................. A61K 31/33
[52] U.S. Cl. .................................................... 424/244
[58] Field of Search ........................ 424/167, 244, 245

Primary Examiner—Stanley J. Friedman
Attorney, Agent, or Firm—Pearne, Gordon, Sessions, McCoy & Granger

[57] ABSTRACT

The present invention is related to pharmaceutical preparations containing as active components the known compound 2-phenyl-1.2-benzisoselenazol-3(2H)-one containing pharmaceutical preparations and process for the treatment in particular of rheumatic diseases.

1 Claim, No Drawings

2-PHENYL-1,2-BENZISOSELENAZOL-3(2H)-ONE CONTAINING PHARMACEUTICAL PREPARATIONS AND PROCESS FOR THE TREATMENT OF RHEUMATIC DISEASES

The present invention is related to pharmaceutical preparations for use in human or veterinary medicine containing the known compound 2-phenyl-1.2-benzisoselenazol-3(2H)-one as active component.

The pharmaceutical preparations according to the present invention may be used for the treatment of many diseases, for instance in the prophylaxis and therapy of infectious diseases, for the therapy of malign tumors, for the stimulation of the immunosystem or in the treatment of diseases caused by selen deficiencies as defined by W. KRAUSS and P. OEHME, Das Deutsche Gesundheitswesen 1979, vol. 34 (3), pgs. 1713 to 1718 and 1979, vol. 34 (37), pgs. 1769 to 1773.

The new pharmaceutical preparations however are characterized by their anti-arteriosclerotic and anti-inflammatory properties. They are in particular useful in the treatment of rheumatic diseases such as arthrosis or chronical polyarthritis. The new pharmaceutical preparations are particularly well compatible since its active agent has a low toxicity and, contrary to known anti-inflammatory agents, does not cause formation of ulcera or gastrointestinal irritations.

The excellent anti-inflammatory properties and the high compatibility of the new pharmaceutical preparations has been determined for instance in the following test methods:

1. The rat pad edema test

The antiphlogistic properties are determined in the rat pad edema test according to HILLEBRECHT (J. HILLEBRECHT, Arzneim. Forsch. 1954, vol. 4, p. 607). In this test, the formation of an edema is caused in one of the hindpads of rats weighing each 200 to 250 grams, by subplantar injection of Carragenine (0.5% in 0.9% NaCl solution) in an amount of 0.1 ml. solution per each pad. After administration of the test compound in an amount which in general should not be larger than a volume of 10 ml. per kg. body weight, the volume of the pad is determined in an overflow. 3 hours after administration of the test compound the final volume is determined. The test is carried out with 10 test animals and 10 control animals of one sex per each dose and is repeated with the same number of animals of the other sex. For evaluation purposes the percent inhibition of edema formation is determined over the control group. The following test values have been determined:

TABLE 1

| | Edema inhibition in rats | | | | | |
|---|---|---|---|---|---|---|
| | 2-Phenyl-1.2-benzisoseleneazol-3(2H)-one | | | Indometacin | | |
| Dose (mg./kg. p.o.) | 0.1 | 1.0 | 10 | 3.8 | 5.6 | 8.3 |
| Inhibitory effect (%) | −1 | −57 | −40 | −26 | −45 | −57 |
| Dose (mg./kg. i.m.) | 0.1 | 1.0 | 10 | 1 | 3 | 10 |
| Inhibitory effect (%) | −23 | −62 | −35 | −9 | −23 | −33 |

2. Granuloma test (cotton-pellet-test) according to R. MEIER et al., Experientia 6, 469 (1950)

In this test, cotton pellets impregnated with crotone oil are implanted subcutaneously into the test animals (rats) which impregnated cotton pellets cause the formation of granuloma in the connective tissue. After killing of the test animals, the granuloma are separated and recovered and are weighed as wet or dry tissue.

The anti-proliferatic activity of an antiphlogistic agent is expressed in a lower granuloma weight in comparison to untreated control animals.

TABLE 2

| | Antiproliferatic activity | | | | | |
|---|---|---|---|---|---|---|
| | 2-Phenyl-1.2-benzisoselenazol-3(2H)-one | | | Indometacin | | |
| Dose (mg./kg. p.o.) | 0.1 | 1 | 10 | 1 | 3.2 | 5.6 |
| Decrease of granuloma weight (%) | −22 | −21 | −20 | −21 | −7 | −6 |

3. Adjunct-Arthritis (C. M. PEARSON, Proc.Soc.exp.Biol. 91, 95-101 (1956)

There are used 10 wistar rats each weighing 120 to 150 g. per each dose. The same number of animals is used as control group. An arthritis is caused by subplantar injection of 0.5 ml. of Freud adjuvans. The test duration is 17 days. At the beginning of the test the volume of the pads of all for legs is determined as starting value. The volume is further determined on the 8th, 14th and 17th day of the test. In the evaluation, the difference between the pad volume at the beginning and at the end of the test is determined both in the test group as well as in the control group. The test result, i.e. the inhibition of the growth of the pad volume is expressed in percent.

TABLE 3

| | Adjunct-Arthritis in rats, p.o. | | | | | |
|---|---|---|---|---|---|---|
| | 2-Phenyl-1,2-benzisoselenazol-3(2H)-one | | | Indometacin | | |
| Dose (mg./kg. p.o.) | 0.1 | 1 | 10 | 0.1 | 1 | 10 |
| inhibitory effect (%) | | | | | | |
| 7th day p.i. | −22 | −46 | −30 | −32 | −50 | lethal |
| 14th day p.i. | −10 | −36 | −22 | −25 | −40 | lethal |
| 17th day p.i. | −13 | −33 | −24 | −37 | −40 | lethal |

The results in Table 3 show that 2-phenyl-1.2-benzisoselenazol-3(2H)-one is characterized by a substantially improved therapeutical range. Even at higher doses no toxicity effects occur.

4. Ulcus test

The determination of ulcus formation is carried out according to W. J. R. WHITTLE, Brit.J.Pharmacology 1975, vol. 55, pgs. 242 to 243; L. MARIANI, Europ. J. Toxicol. Eviron, 1975, vol. 8, pgs. 335 to 339; R. MENGUY and L. DESBAILLETS, Proc.Soc.Exp.Bio., vol. 125, p. 1108. In this test, 10 female and 10 male wistar rats are used each weighing 120 to 150 g. and which had been fed only with hydrocarbons for 2 days and were kept thereafter without feeding for 16 hours. The formation of a bleeding ulcus of the stomach was provocated by oral application of the compound to be tested. 3.5 hours after administration the test animals were killed, the stomach was separated, opened along the large curvature and fixed to a polystyrol plate. There is determined the number and size of average ulcus formation both in the test group and in the control group. All known antiphlogistics which can be used therapeutically and do not represent a steroid produce ulceration of the mucous membrane of the stomach under these conditions within the therapeutical dose range.

TABLE 4

| Ulcus formation in rats | | | | | | |
|---|---|---|---|---|---|---|
| | 2-Phenyl-1.2-benzoisoselenazol-3(2H)-one | | | Indometacin | | |
| Dose (mg./kg. p.o.) | 1 | 10 | 100 | 3.2 | 5.6 | 7.5 |
| effectiveness | 0 | 0 | 0 | ++ | +++ | +++ |

0 = no ulcus formation
+ = moderate ulcus formation
++ = considerable ulcus formation
+++ = very strong ulcus formation

TABLE 5

| Toxicity | | |
|---|---|---|
| | 2-Phenyl-1.2-benzisoselenazol-3(2H)-one | Indometacin |
| (a) in rats, p.o. | | |
| dose (mg./kg.) | 4,600 | 38 |
| lethality (%) | 0 | 50 |
| (b) in mice, p.o. | | |
| dose (mg./Kg.) | >2,150 | 19 |
| lethality (%) | 0 | 50 |

The active compound 2-phenyl-1.2-benzisoselenazol-3(2H)-one is known as such (see for instance Ber. 57 (1924) p. 1080) and may be produced by processes known as such (R. WEBER and M. RENSON, Bulletin de la Soc. Chim. de France 1976 (7/8), pgs. 1124 to 1126) by subjecting 2-methylseleno-N-phenyl-benzamid to reaction with phosphorus pentachloride ,nd subjecting the resulting product to hydrolysis.

For producing the new pharmaceutical preparations according to the present invention containing 2-phenyl-1.2-benzisoselenazol-3(2H)-one as active component, this active component may be used as such or in combination with usual pharmaceutical carrier materials and may be formulated as usual. For use in human or veterinary medicin, the active compound may be applied in any known form as long as the formation and maintenance of a sufficient blood or tissue level is obtained thereby. Thus, this is possible after oral or rectal or parenteral administration of a suitable dose. Pharmaceutical preparations for single dosage administrations are preferred such as tablets, dragees, capsules, suppositories, granulates, solutions, emulsions, suspensions, soles or gels. The dose in general is between 10 and 1,000 mg. per day, preferably between 30 and 300 mg. per day and may be administered in a single or in several dosages, preferably in two or three dosages per day.

Suitable carrier materials which may be used for pharmaceutical preparations to be administered orally such as tablets, capsules, granulates or powders, are calcium carbonate, calcium phosphate, starch, sugar, lactose, talcum, magnesium stearate, gelatine, polyvinylpyrrolidone, gum arabic, sorbitol, microcristalline cellulose, polyethyleneglycol, carboxymethyl cellulose, shellac or the like. Tablets may be coated in usual manners. Liquid pharmaceutical preparations for oral administrations may be aqueous or oily suspensions or solutions, sirups or the like. They are produced in usual manners. Injectable preparations may be aqueous or oily suspensions or solutions, powderous products containing a filler or lyophilised products which are dissolved before administration. These products are also produced in known manners.

The pharmaceutical products according to the present invention may also be suppositories for rectal administration which may contain pharmaceutically acceptable carrier materials as they are known for this purpose, for instance polyethylene glycol, lanoline, coconut butter, Witepsol ® or the like. External pharmaceutical preparations are preferably produced as ointments or cremes in usual manners using usual components.

EXAMPLE 1

| Tablets | |
|---|---|
| 2-phenyl-1.2-benzisoselenazol-3(2H)-one | 30 mg. |
| lactose | 150 mg. |
| cristalline cellulose | 50 mg. |
| calciumcarboxymethyl cellulose | 7 mg. |
| magnesium stearate | 3 mg. |

The above components are mixed and pressed to tablets in a usual manner using usual equipment. If desired, the tablets may be coated with a usual coating.

EXAMPLE 2

| Tablets | |
|---|---|
| 2-phenyl-1.2-benzisoselenazol-3(2H)-one | 50 mg. |
| microcristalline cellulose | 150 mg. |
| Cutina HR | 15 mg. |
| hydroxypropylmethyl cellulose phthalat | 20 mg. |

EXAMPLE 3

| Capsules | |
|---|---|
| 2-phenyl-1.2-benzisoselenazol-3(2H)-one | 30 mg. |
| lactose | 102 mg. |
| cristalline cellulose | 56 mg. |
| kolloidal silica | 2 mg. |

The above components are mixed and granulated as usual and filled into hard gelatine capsules.

EXAMPLE 4

| Capsules | |
|---|---|
| 2-phenyl-1.2-benzisoselenazol-3(2H)-one | 50 mg. |
| talcum | 5 mg. |
| aerosil 200 | 10 mg. | are mixed, granulated and filled into hard gelatine capsules.

What we claim is:
1. A process for the treatment of rheumatic diseases comprising administering to a being suffering from such disease 2-phenyl-1.2-benzisoselenazol-3(2H)-one and, optionally, a carrier material therewith, in an amount ranging from 10 to 1000 mg per day.

* * * * *